(12) United States Patent
Reddy (10) Patent No.: US 8,748,484 B2
(45) Date of Patent: Jun. 10, 2014

(54) ORGANOMETALLIC ANTI-CANCER COMPLEXES

(75) Inventor: Varattur Dayal Reddy, Oakland Gardens, NY (US)

(73) Assignee: Research Foundation of The City University of New York, New York, NY (US)

( * ) Notice: Subject to any disclaimer, the term of this patent is extended or adjusted under 35 U.S.C. 154(b) by 0 days.

(21) Appl. No.: 14/110,357

(22) PCT Filed: Apr. 9, 2012

(86) PCT No.: PCT/US2012/032800
§ 371 (c)(1),
(2), (4) Date: Oct. 7, 2013

(87) PCT Pub. No.: WO2013/112186
PCT Pub. Date: Aug. 1, 2013

(65) Prior Publication Data
US 2014/0031565 A1 Jan. 30, 2014

Related U.S. Application Data

(60) Provisional application No. 61/472,977, filed on Apr. 7, 2011.

(51) Int. Cl.
*C07D 309/32* (2006.01)
*A61K 31/351* (2006.01)

(52) U.S. Cl.
USPC ............ 514/460; 549/356; 549/415; 514/451

(58) Field of Classification Search
USPC .......................... 549/356, 415; 514/451, 460
See application file for complete search history.

(56) References Cited

U.S. PATENT DOCUMENTS 5,824,673 A * 10/1998 Abrams et al. ................ 514/184
6,417,182 B1 * 7/2002 Abrams et al. ................ 514/184

OTHER PUBLICATIONS

Reddy, V.D. et al., Glycal-ruthenium carbonyl clutsters: Syntheses, characterization, and anticancer activity, Journal of Organometallic Chemistry, 2009, vol. 694, pp. 959-967.
Reddy, V.D., Synthesis, characterization, and reactivity of a novel ruthenium carbonyl cluster containing tri-O-benzyl-D-Glucal as a chiral carbohydrate ligand, Journal of Organometallic Chemistry, 2006, vol. 691, pp. 27-34.
Kandioller, Wolfgang et al., From Pyrone to Thiuopyrone Ligands-Rendering Maltol-Derived Ruthenium(II)-Arene Complexes That are Anticancer Active in Vitro, Organometallics, 2009, vol. 28, pp. 4249-4251.
Kandioller, Wolfgang et al., Tuning the anticancer activity of maltol-derived ruthenium complexes by derivatization of the 3-hydroxy-4-pyrone moiety, Journal of Organometallic Chemistry, vol. 694, pp. 922-929, 2009.
Kandioller, Wolfgang et al., Maltol-Derived Ruthenium-Cymene Complexes with Tumor Inhibiting Properties: The Impact of Ligand-Metal Bond Stability on Anticancer Activity in Vitro, Chem. Eur. J. 2009, vol. 15, pp. 12283-12291.

* cited by examiner

*Primary Examiner* — Golam M M Shameem
(74) *Attorney, Agent, or Firm* — Hoffmann & Baron, LLP.

(57) ABSTRACT

An anti-cancer ruthenium complex containing organometallic triruthenium with two maltol ligands is claimed.

12 Claims, 4 Drawing Sheets

ORGANOMETALLIC ANTI-CANCER COMPLEXES

CROSS-REFERENCE TO RELATED APPLICATIONS

This application is a U.S. National Phase Application of International Application No. PCT/US2012/032800 filed on Apr. 9, 2012 and asserts priority to U.S. Provisional Application No. 61/472,977 on Apr. 7, 2011, all of which are hereby incorporated by reference in their entirety.

FIELD OF THE INVENTION

This invention relates to an anti-cancer ruthenium complex.

BACKGROUND OF THE INVENTION

Currently, there is great interest in the synthesis of organometallic compounds as anticancer agents.[1] In recent years, several ruthenium-based compounds have attracted attention due to their promising anticancer activity.[2-7] Cisplatin and its derivatives are already widely used in the clinic as anticancer agents. Nonetheless, these drugs have severe toxic side effects, are inactive against certain cancers, and can often develop resistance to tumors.[8-11] Therefore the quest for innovative organometallic drugs are in increasing demand.

Maltol, a 4-pyrone (2-methyl-3-hydroxy-4-pyrone) (L) has antioxidative[14] and iron chelating properties.[15] Pyrones are bioactive compounds present in many natural products such as steroids, kojic acid, and anticoagulant warfarin and a class of important metal chelators with versatile medicinal applications. Hartinger and his coworkers have reported maltol-derived ruthenium(II)-arene complexes that are anticancer active in vitro.[16]

There is a need for new organometallic compounds that can be used as anticancer agents.

SUMMARY OF THE INVENTION

An anti-cancer ruthenium complex is provided. The complex has the formula 1:

wherein:
$R^1$ independently represents —H, —$CH_3$, or —$CH_2CH_3$;
$R^2$ independently represents —H, —$CH_3$, —$CH_2CH_3$, —$CH_2OH$, —$CH_2SH$, —$SCH_3$, —$SCH_2CH_3$, —$OCH_3$, —$OCH_2CH_3$, —S-carbocycloalkyl, —O-carbocycloalkyl, —S-aryl, —O-aryl, —S-benzyl, —O-benzyl, or —C(O)NHCH$_2$aryl;
n independently represents 0 or 1;
when n represents 1, X independently represents O, S, or $NR^3$;
when n represents 0, a single bond exists between the two carbon atoms adjacent to (X)
$R^3$ independently represents —H, —$CH_3$, or —$CH_2CH_3$;
Y independently represents O or S
Z independently represents O, S, or $NR^4$:
$R^4$ independently represents —H or —$CH_3$;
L represents a carbonyl, $Ph_3P$, imidazole, thiazole, oxazole, or indazole moiety; or an N-heterocyclic carbene moiety selected from the group consisting of 1,3-imidazol-2-ylidene substituted independently at 1,3 atoms; 1,2,4-triazol-5-ylidene substituted independently at 1,4 atoms; or 1,2,3-triazol-5-ylidene substituted independently at 1,4 atoms; wherein the N-heterocyclic carbene moiety is substituted by a substituent selected independently from the group consisting of aryl, benzyl, $C_{1-6}$ alkyl, or cyclohexyl;
aryl is selected from the group consisting of phenyl or a 5 or 6 member heterocyclic aromatic ring comprising at least one ring heterocyclic atom or group selected from the group consisting of —O—, —S—, —NH—, or —$NCH_3$—;
carbocycloalkyl groups are 5 or 6 member non-aromatic carbocyclic rings;
aryl and carbocycloalkyl groups independently are unsubstituted, or are substituted at any position with one or more substituents;
aryl substituents independently are $R^{10}$, —$OR^{11}$, —$SR^{11}$, —$N(R^{11})_2$, $R^{10}C(O)$—, nitro, or halo (F, Cl, or Br), wherein $R^{10}$ independently represents aryl, $C_{1-6}$ alkyl or cyclohexyl; and $R^{11}$ independently represents H, aryl, $C_{1-6}$ alkyl or cyclohexyl; and
carbocycloalkyl substituents independently are $C_{1-6}$ alkyl.

In a preferred embodiment, L represents a carbonyl.
In another preferred embodiment Y is O.
In yet another preferred embodiment, n is 1 and X is O.
In yet another preferred embodiment $R^1$ is —H or —$CH_3$.
In yet another preferred embodiment $R^1$ is —$CH_3$.
In yet another preferred embodiment $R^2$ is —H or —$CH_3$.
In yet another preferred embodiment $R^2$ is —H.
In yet another preferred embodiment Z is O.
In yet another preferred embodiment n is 1 and X is S.
In yet another preferred embodiment n is 1, X is O, Y is O, Z is O, $R^1$ is —$CH_3$, $R^2$ is —H, and L is carbonyl.

DETAILED DESCRIPTION OF EMBODIMENTS

The invention relates to an anti-cancer ruthenium complex having formula 1:

An alternative way of showing formula 1 is:

where the coordinate bond is shown between Y and Ru in formula 1a.

In formula 1, $R^1$ independently represents —H, —$CH_3$, or —$CH_2CH_3$. In a preferred embodiment, $R^1$ is —H or —$CH_3$.

In formula 1, $R^2$ independently represents —H, —$CH_3$, —$CH_2CH_3$, —$CH_2OH$, —$CH_2SH$, —$SCH_3$, —$SCH_2CH_3$, —$OCH_3$, —$OCH_2CH_3$, —S-carbocycloalkyl, —O-carbocycloalkyl, —S-aryl, —O-aryl, —S-benzyl, —O-benzyl, or —$C(O)NHCH_2$aryl. $R^2$ is preferably —H or —$CH_3$.

The letter n independently represents 0 or 1. When n represents 1, X independently represents O, S, or $NR^3$. When n represents 0, a single bond exists between the two carbon atoms adjacent to (X). Therefore, a five member ring is formed. In the example below, n represents 0 in the top ligand, and n is 1 and X is O in the bottom ligand.

$R^3$ independently represents —H, —$CH_3$, or —$CH_2CH_3$. $R^3$ is preferably —H or —$CH_3$.

Y independently represents O or S. Y is preferably O.

Z independently represents O, S, or $NR^4$. Z is preferably O. $R^4$ independently represents —H or —$CH_3$.

The ligand L represents a moiety that is bonded to the ruthenium atom in formula 1 that is not bonded to Z. This ruthenium atom will be referred to as the distal ruthenium atom. Some suitable L groups include, for example, a carbonyl, $Ph_3P$, imidazole, thiazole, oxazole, or indazole moiety. L is preferably a carbonyl.

Alternatively, L represents an N-heterocyclic carbene moiety selected from the group consisting of 1,3-imidazol-2-ylidene substituted independently at 1,3 atoms; 1,2,4-triazol-5-ylidene substituted independently at 1,4 atoms or 1,2,3-triazol-5-ylidene substituted independently at 1,4 atoms. The N-heterocyclic carbene moieties are substituted by a substituent selected from the group consisting of aryl, benzyl, $C_{1-6}$ alkyl, or cyclohexyl groups. The N-heterocyclic carbene moieties 1,3-disubstituted-1,3-imidazol-2-ylidene; 1,4-disubstituted-1,2,4-triazol-5-ylidene; and 1,4-disubstituted-1,2,3-triazol-5-ylidene may be represented, respectively, as follows wherein $R^a$ and $R^b$ are the substituents:

The nature of the bond between L and the distal ruthenium atom in formula 1 is not critical, and may, for example, be a covalent bond, a coordinate bond, or a bond with characteristics of both covalent and coordinate bonds. It is believed that carbonyl moieties are bonded to the distal ruthenium atom by means of a coordinate bond with a sigma donation from the carbonyl carbon and some pi bonding from the metal to the carbonyl carbon atom. The carbene carbon atom between two nitrogen atoms of N-heterocyclic carbene moieties are believed to be bonded to the distal ruthenium atom through a single sigma bond with some back bonding from Ru. Imidazole and indazole moieties are believed to be bonded to the distal ruthenium atom by means of a coordinate bond with a saturated nitrogen atom. Thiazole and oxazole moieties are believed to be bonded to the distal ruthenium atom by means of a coordinate bond with a nitrogen atom as a major product (approximately 95% or more) and a coordinate bond with sulfur or oxygen, respectively, as a minor product (approximately 5% or less).

An aryl group is selected from the group consisting of phenyl and a 5 or 6 member heterocyclic aromatic ring comprising at least one ring heterocyclic atom or group, typically 1-3 ring heterocyclic atoms or groups. The ring heterocyclic atom or group is selected from —O—, —S—, —NH—, or —$NCH_3$—. The preferred aryl group is phenyl. Examples of 5 or 6 member heterocyclic aromatic rings include thiophenyl, furyl, pyrrolyl, pyrazolyl, imidazolyl, oxazolyl, thiazolyl, pyridinyl, pyridazinyl, pyrimidinyl, and pyrazinyl.

Carbocycloalkyl groups are 5 or 6 member non-aromatic carbocyclic rings. Examples of carbocycloalkyl groups are cyclopentyl and cyclohexyl groups.

Aryl and carbocycloalkyl groups independently are unsubstituted, or are substituted at any position with one or more substituents. Aryl substituents independently are $R^{10}$, —$OR^{11}$, —$SR^{11}$, —$N(R^{11})_2$, $R^{10}C(O)$—, nitro, or halo (F, Cl, or Br). $R^{10}$ independently represents aryl, $C_{1-6}$ alkyl or cyclohexyl; and $R^{11}$ independently represents H, aryl, $C_{1-6}$ alkyl or cyclohexyl. Carbocycloalkyl substituents independently are $C_{1-6}$ alkyl.

$C_{1-6}$ alkyl groups may be branched or unbranched. Some examples of $C_{1-6}$ alkyl groups include methyl, ethyl, n-propyl, isopropyl, n-butyl, t-butyl, n-pentyl, isopentyl, and n-hexyl groups.

Any of the aryl and carbocycloalkyl groups may be unfused or fused. Some examples of fused aryl groups include naphthyl, phenanthryl, anthracenyl, triphenylenyl, chrysenyl, pyrenyl, purinyl, 1,4-diazanaphthalenyl, indolyl, benzimidazolyl, 4,5-diazaphenanthrenyl, and benzoxazolyl.

The compounds of the invention may be made by any method known in the art. For example, compounds 1-4 were made and characterized by the methods discussed below.

Synthesis and Characterization of Ruthenium-maltol Complexes

Compounds 1-4 were prepared to study their antitumor activity. Compounds 2-4 were prepared from 1 by substituting a CO group with triphenylphosphine, 2, 1,1-bis(diphenylphosphinomethane), dppm, 3, 1,2-bis(diphenylphosphinoethane), dppe, 4, respectively. The four complexes were characterized by IR and NMR spectroscopy, mass Spectrometry, and elemental analysis; compounds 1 and 2 were characterized by single-crystal X-ray crystallography as well. The reaction of $Ru_3(CO)_{12}$ with two equivalents of maltol at octane reflux temperature to give a novel cluster 1, $Ru_3(CO)_8$(2L-2H) (L=Maltol) exclusively as a yellow solid as shown in Scheme 1.

Scheme 1 Synthesis of $Ru_3(CO)_8$(2L-2H) (L = Maltol), 1.

Figure 1:
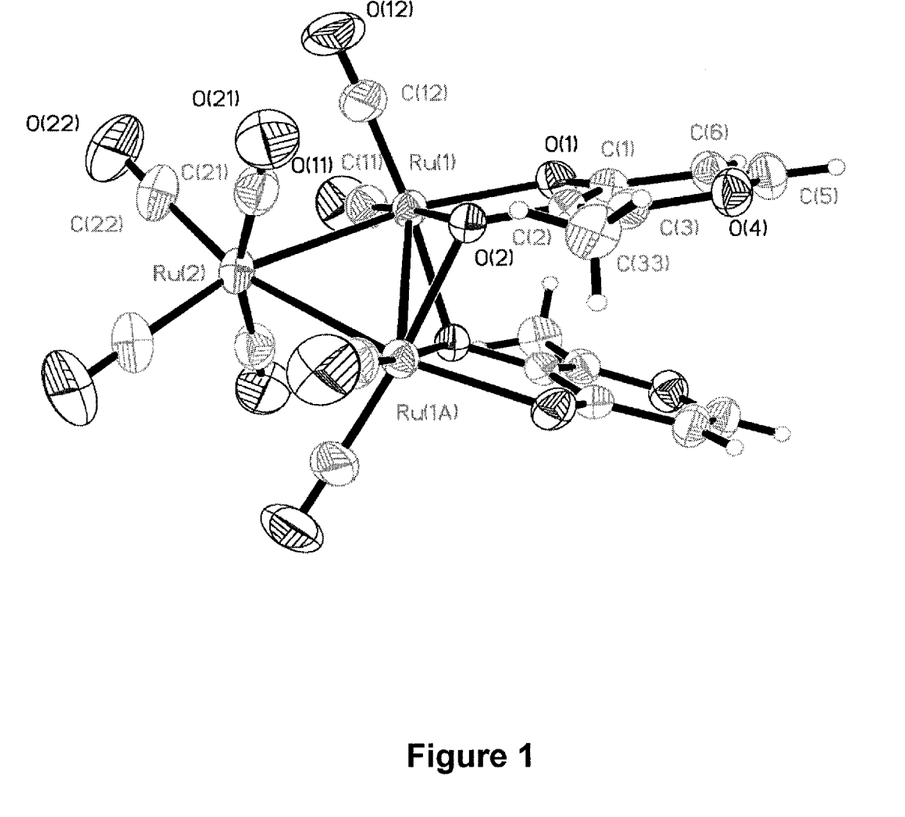
FIG. 1 is an ORTEP diagram (50% probability thermal ellipsoids) of Compound 1, $Ru_3(CO)_8(C_6O_3H_5)_2$.

The cleavage of the O—H bond of the hydroxyl group in maltol is favored over orthometallation giving the cluster 1 as the only product. No orthometallation product is isolated in this reaction and no hydride is located in the hydride region of $^1$H NMR spectra. Yellow crystals of 1 were obtained by slow evaporation of dichloromethane-diethyl ether mixture, and the structure was determined by X-ray crystallography. The ORTEP diagram of the molecular structure of 1 and atomic numbering scheme is shown in FIG. 1.

The molecule of $Ru_3(CO)_8(C_6H_5O_3)_2$ 1 has a crystallographic two-fold axis which relates Ru(1) to Ru(1A) and upon which Ru(2) sits. The labeled atoms of the coordinated $C_6H_5O_3^{-1}$ ligand are related to the unlabeled $C_6O_3H_5^{-1}$ by this two-fold axis. The $C_6H_5O_3^{-1}$ ligand is coordinated in a bidentate fashion to Ru(1) through O(1) and the dehydrogenated O(2) atoms. O(2) is also coordinated to Ru(1A) thus it also bridges Ru(1) and Ru(1A). The two $C_6H_5O_3^{-1}$ ligands are stacked with each other in a head to tail manner. The angle between the best planes is 27.1°. The two maltol ligands span the same Ru(1)-Ru(1A) edge with each ruthenium containing two carbonyl ligands, while Ru(2) has four carbonyl ligands. The angle formed between the plane of the three ruthenium atoms and the best plane of the $C_6H_5O_3^{-1}$ ligand is 40.2°. Table 1 contains a list of selected bond distances and angles for 1.

TABLE 1

Selected bond lengths [Å] and angles [°] for 1, $Ru_3(CO)_8(C_6O_3H_5)_2$.

| | |
|---|---|
| Ru(1)—C(11) | 1.834(2) |
| Ru(1)—O(2) | 2.1310(12) |
| Ru(1)—O(1) | 2.1775(13) |
| Ru(1)—O(2)#1 | 2.1994(12) |
| Ru(1)—Ru(2) | 2.7626(2) |
| Ru(1)—Ru(1)#1 | 3.0287(3) |
| O(1)—C(1) | 1.269(2) |
| O(4)—C(5) | 1.340(3) |
| C(5)—C(6) | 1.331(3) |
| C(12)—Ru(1)—C(11) | 86.85(10) |
| C(12)—Ru(1)—O(2) | 97.91(8) |
| C(22)—Ru(2)—C(21)#1 | 94.31(11) |
| C(22)—Ru(2)—C(21) | 95.66(11) |
| C(21)#1—Ru(2)—C(21) | 164.49(13) |
| Ru(1)#1—Ru(2)—Ru(1) | 66.483(8) |

Symmetry transformations used to generate equivalent atoms: #1 −x + 1, y, −z + 1/2

The Ru(1)-CO bond lengths average 1.832(2) Å while the Ru(2)-CO bond lengths are significantly longer at an average of 1.937(4) Å. The two maltol ligands are bound to the cluster core through their two exocyclic oxygen atoms (C=O and OH oxygens). The H-atom cleaved from the O—H bond of the hydroxyl group and then the dehydrogenated hydroxyl is bonded to the ruthenium metal. The likely pathway for the formation of 1 involves an oxidative addition of the OH bond of maltol to the triruthenium cluster to form a monohydride followed by a second oxidative addition of second maltol OH bond to form an intermediate dihydride which then undergoes hydrogen elimination.[17] Thus the molecule contains a triangular cluster of three ruthenium atoms with two bridging maltol ligands binding to a Ru—Ru bond by their two exocyclic oxygen atoms in a $\mu$-$\eta^2$-bonding mode. The two ruthenium atoms bridged by maltol ligands have two carbonyl ligands each and the third ruthenium is bonded to four carbonyl ligands. The coordination of the $C_6H_5O_3^{-1}$ ligand in 1 is somewhat similar to that observed in $Os_3(CO)_9(\mu$-H$)(\mu$-4-$C_6O_3H_5)$[18] but in 1 the second $C_6H_5O_3^{-1}$ ligand replaces one CO and the bridging hydrogen. In compounds 1 and $Os_3$ $(CO)_9$ ($\mu$-H$)(\mu$-$\gamma$-$C_6H_5O_3)$ two metal atoms are seven coordinate while the third metal atom is six coordinate, and in both 1 and $Os_3(CO)_9(\mu$-H$)(\mu$-4-$C_6H_5O_3)$[18] both the M-CO trans to a coordinated O is shorter than the other M-CO bonds. In 1 the doubly bridged Ru—Ru bond is longer by 0.26 Å than the other Ru—Ru bonds while in the singly bridged Os complex $Os_3(CO)_9(\mu$-H$)(\mu$-4-$C_6H_5O_3)$ all Os—Os bonds are about the same. The Ru—Ru bond distances in 1 span a large range, with Ru(1)-Ru(2) being the shortest at 2.7626(2) Å and Ru-(1)-Ru(1A) being very long at 3.0287(3) Å, which is comparable to the following clusters. The trinuclear cluster $Ru_3$ $(CO)_8(\mu$-CO$)(\mu$-H$)[\mu$-$\eta^3$-($\eta^5$-$C_5H_3$PFcPh)Fe($\eta$5-$C_5H_5$)][19] in which the Ru(1)-Ru(3)=2.7817(6) Å, Ru-(1)-Ru(2)=3.0316(7) Å; in $(\mu$-H$)_2Ru_4(CO)_{12}(\mu$-PPh$)$[20] the long- est metal-metal bond Ru(3)-Ru(1)=3.006(1) Å. Interestingly, the Ru—Ru bond from the silyl-substituted ruthenium atom to the apical ruthenium atom is unusually long, 3.1353(8) Å in $Ru_5(CO)_{14}(SiEt_3)(\mu_5\text{-}C)(\mu\text{-}H)$.[21]

The IR spectrum of 1 shows terminal carbonyl stretching at 2091 (s), 2020 (s, sh), 1926 (s) cm$^{-1}$ and stretching absorptions at 1615 (s), 1574(s), 1510(s), 1469 (m) cm$^{-1}$ due to coordinated maltol ligands. The stretching absorptions of coordinated maltol shifted to lower wave numbers when compared to free maltol ligand stretching absorptions at 1670 (m), 1635 (s, sh), 1569 (m) indicating that maltol is a strong donor ligand. The $^1$H NMR spectrum of free maltol was recorded in $CD_2Cl_2$ in order to assign resonances for bound maltol (see supplemental material). The $^1$H NMR spectrum of 1 in $CD_2Cl_2$ shows a doublet at δ 7.61 ($^3J_{C\text{-}H}$=5.7 Hz) due to the hydrogen bonded to C6 and a doublet at δ 6.26 ($^3J_{C\text{-}H}$=5.7 Hz) is due to the hydrogen bonded to C5. The singlet at δ 2.53 is due to the methyl group bonded to C2. The broad resonance due to the hydroxyl hydrogen in free maltol at δ 7.03 was not found in the cluster bound maltol indicating that hydrogen is apparently lost upon binding to cluster and no hydride resonance in $^1$H NMR was observed in the hydride region. The $^1$H resonances at C6 and C5 are shifted upfield 0.1 ppm where as $^1$H resonances for methyl group shifted upfield 0.2 ppm (when compared to $^1$H resonances of the free maltol). ESI-APCI mass spectrum shows a cluster of peaks centered at 779.7302 corresponding to MH$^+$. The isotopic distribution pattern is consistent with the presence of three ruthenium atoms. Compound 1 contains 48 valence electrons at the metal atoms with 2L-2H donating 8 electrons, the eight CO groups contribute 16 electrons, and the three ruthenium atoms contribute a total of 24 electrons. 48 electrons are expected for trinuclear cluster containing three metal-metal bonds.

The compound $Ru_3(CO)_8(2L\text{-}2H)$ 1 (L=maltol) has a unique ruthenium atom Ru(2) with significantly longer CO bond distances than the other two ruthenium atoms as revealed by X-ray crystallography. Thus, compound 2 was prepared by the reaction of compound 1 with 1.0 equivalent of triphenylphosphine in the presence of $Me_3NO.2$; $H_2O$ to assist the removal of a carbonyl ligand in dichloromethane solution at room temperature as shown in Scheme 2.

Scheme 2 Synthesis of $Ru_3(CO)_7PPh_3(2L\text{-}2H)$ (L = Maltol), 2.

Figure 2:
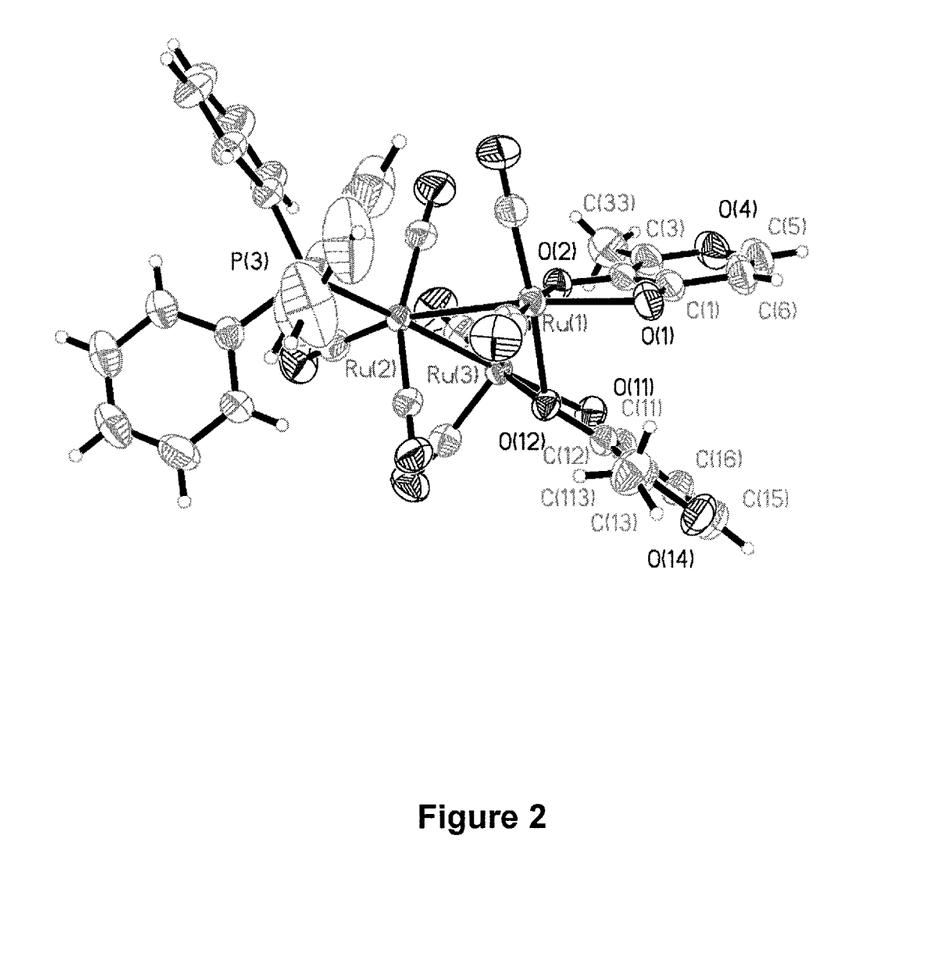
FIG. 2 is an ORTEP diagram (50% probability thermal ellipsoids) of Compound 2, $Ru_3(CO)_8PPh_3(C_6O_3H_5)_2$.

Compound 2 was isolated in pure form by preparative thin layer chromatography on silica gel with a dichloromethane solvent and was characterized by spectroscopic techniques, and single-crystal X-ray diffraction analysis. Yellow crystals of the solvate 2. $0.5CH_2Cl_2$ were grown by layering hexane on a solution of 2 in dichloromethane at −10° C. A single-crystal X-ray diffraction study was undertaken in order to discern which carbonyl group in 1 was substituted by triphenylphosphine. There are two independent but structurally similar complexes in the asymmetric unit. An ORTEP diagram of the molecular structure of 2 is shown in FIG. 2. Selected bond distances and angles are given in Table 2.

TABLE 2

| Selected bond lengths [Å] and angles [deg] for Complex 2. | |
|---|---|
| Ru(1)—C(111) | 1.821(5) |
| Ru(1)—C(112) | 1.830(5) |
| Ru(1)—O(2) | 2.137(3) |
| Ru(1)—O(12) | 2.196(3) |
| Ru(1)—O(1) | 2.210(3) |
| Ru(1)—Ru(2) | 2.7850(4) |
| Ru(1)—Ru(3) | 3.0320(4) |
| C(111)—Ru(1)—C(112) | 87.0(2) |
| C(111)—Ru(1)—O(2) | 96.57(19) |
| C(112)—Ru(1)—O(2) | 176.38(17) |
| C(111)—Ru(1)—O(12) | 170.30(18) |
| C(25)—Ru(2)—P(3) | 97.82(14) |
| P(3)—Ru(2)—Ru(3) | 177.09(3) |
| C(26)—Ru(2)—Ru(1) | 157.56(13) |
| P(3)—Ru(2)—Ru(1) | 112.91(3) |
| Ru(3)—Ru(2)—Ru(1) | 66.295(11) |
| C(32)—Ru(3)—O(2) | 96.97(18) |
| O(12)—Ru(3)—O(2) | 77.19(11) |

Symmetry transformations used to generate equivalent atoms: −x + 1, y, −z + 1/2

The complex 2 contains a triangle of three ruthenium atoms bridged by two dehydrogenated maltol ligands span the same Ru—Ru edge and two carbonyl ligands bonded to each of the two ruthenium atoms. The third unique ruthenium atom is bonded to three carbonyl ligands and a triphenylphosphine ligand occupying an equatorial site. The triphenylphosphine replaces one of the equatorial carbonyl ligand in 1 at unique Ru(2); that is in 1 Ru(2)-CO bond lengths are significantly longer at an average of 1.937(4) Å than the other two Ru—CO bond lengths average 1.832(2) Å. In 2 the equatorial Ru(2)-CO bond length is 1.886(4) while the two axial Ru(2)-CO bond lengths average 1.924 (4); this difference in bond distances are due to the substitution of a equatorial carbonyl ligand by a triphenylphosphine at Ru(2). The Ru—P bond distance 2.376(10) is comparable to other structurally characterized triruthenium clusters containing phosphmes.[13,22] The greatest structural difference between 1 and 2 is in the angle between the best planes of the two coordinated $C_6H_5O_3^{-1}$ ligands. In 1 it is 27.1° while in 2 it is 42.8°. The angle formed between the best plane formed by the three ruthenium atoms and the best plane of the $C_6H_5O_3^{-1}$ ligand is 40.2° in 1 and 44.1° and 45.4° in 2. Table 2 contains a list of select bond distances and angles for 1 and 2. The Ru(1)-CO bond lengths average 1.832(2) in 1 and 1.829(5) in 2 Å while the Ru(2)-CO bond lengths are significantly longer at an average of 1.937(4) in 1 and 1.911(5) in 2 with Ru2-C26 being 1.886(5) Å.

The IR spectrum of 2 in dichloromethane shows C—H stretching at (several bands due to maltol ligand and triphenyl phosphine), terminal carbonyl stretching: 2045 (w), 1991 (vs), 1970 (s), 1913 (m) and C—O stretching due coordinated maltol ligands: 1616 (m), 1578 (w), 1513 (w). The $^1$H NMR spectrum of 2 in $CD_2Cl_2$ shows resonances at δ 7.62 and δ 7.43 due to phenyl groups, distorted doublet at δ 7.65 due to the hydrogen bonded to C6 which is partially overlapping with the resonances for phenyl groups at 7.62, two doublets at δ 6.21 ($^3J_{C-H}$=5.0 Hz), 6.17 ($^3J_{C-H}$=5.0 Hz) are due to the hydrogens bonded to C5 in two maltol ligands that are inequivalent due to phosphine substitution at Ru(3) of compound 1, and the singlet at δ 2.53 is due to the methyl group bonded to C2. $^{31}$P NMR shows a singlet at δ 30.2 due the triphenylphosphine bonded to Ru(2). The ESI-APCI mass spectrum shows M$^+$ peak at 1012.8164. The spectroscopic data is consistent with the single-crystal X-ray structure.

Compound 3 was prepared at room temperature from the reaction of 1 with bis(diphenylphosphino)methane(dppm) in the presence of $Me_3NO.2;H_2O$. as shown in Scheme 3.

tiplet at δ 7.0-7.2 due to 12H and a multiplet at δ 7.3-7.4 due to 8H for four maltol ligands, two singlets at δ 2.38 and δ 2.46 integrating to 6H each are due to four methyl groups, a pseudo triplet at δ 4.05 is due to two hydrogens which is part of bridging dppm ligand $PCH_2P$ indicating that the dppm ligand coordinated to two equivalent molecules of compound 1 by their phosphine atoms replacing one CO ligand at each Ru(2) atom to form compound 3. $^{31}$P NMR shows a two singlet δ 23.40 and δ 23.09 due the dppm bonded to two Ru(2) atoms. The ESI-APCI mass spectrum shows a molecular ion (M$^+$) peak at 1883.5659 suggests a dimer of compound 1 bridged by a dppm ligand; that is, indicating two identical $Ru_3(CO)_7$ $(C_{12}H_{10}O_6)$ moieties bridged by a dppm ligand. The spectroscopic data is consistent with the possible structure shown in scheme 3.

Compound 4 was prepared from the reaction of 1 with 1,2-bis(diphenylphosphino)ethane (dppe) at room temperature in the presence of $Me_3NO.2H_2O$, Several attempts to grow single crystals resulted in a yellow powder. The IR spectrum of 4 in dichloromethane shows C—H stretching (several bands due to maltol and phosphine) 3052 (m), 2958 (w), 2858 (w); terminal carbonyl stretching: 2047 (w), 1989 (vs, sh), 1970 (s), 1911 (m); C—O stretching due coordinated maltol ligands: 1616 (m), 1578 (w), 1512 (w). The $^1$H NMR spectrum of 4 in $CDCl_3$ shows a doublet at δ 7.47 ($^3J_{C-H}$=5.7 Hz) due to the hydrogen bonded to C6 and a doublet at δ 6.05 ($^3J_{C-H}$=5.7 Hz) is due to the hydrogen bonded to C5. A mul- Scheme 3 Synthesis of $[Ru_3(CO)_7 (2L-2H)]_2$(dppm or dppe) (L = Maltol), 3 and 4.

n = 1 dppm 3
n = 2 dppe 4

Several attempts to grow single crystals in different solvents and at different temperatures yielded plated like crystals and intertwined crystals that did not diffract well. The IR spectrum of 3 in dichloromethane shows C—H stretching (several bands due to maltol and phosphines) 3052 (m), 2958 (w), 2858 (w); terminal carbonyl stretching: 2047 (w), 1992 (vs), 1979 (s), 1914 (m); C—O stretching due coordinated maltol ligands: 1616 (m), 1578 (w), 1515 (w). The $^1$H NMR spectrum of 3 in $CD_2Cl_2$ shows a doublet at δ 7.47 ($^3J_{C-H}$=5.7 Hz) due to the hydrogen bonded to C6 and a doublet at δ 6.15 ($^3J_{C-H}$=5.7 Hz) is due to the hydrogen bonded to C5. A multiplet at δ 7.0-7.2 due to 12H and a multiplet at δ 7.3-0.4 due to 8H for four maltol ligands, indicating that the dppe ligand coordinated to two molecules of compound 1 by their phosphine atoms replacing one CO ligand at each Ru(2) atom from 1. Two singlets at δ 2.38 and δ 2.46 each integrating 6H each are due to four methyl groups in compound 2. A multiplet at δ 3.43-3.72 is due to four hydrogens which is part of bridging dppe ligand $PCH_2CH_2P$. $^{31}$P NMR in $CDCl_3$ shows a two singlets at δ 23.82, 23.79 due the dppe bonded to two Ru(2) atoms similar to compound. The mass spectrum is consistent with formulation given. The ESI-APCI mass spectrum shows molecular ion peak (M⁺) peak at 1897.5847 due to a dimer of compound 1 bridged by a dppe ligand. The spectroscopic data is consistent with the proposed structure in Scheme 3.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. $R^1$, $R^2$, $R^3$, $R^4$, n, Y, and Z). Each group contains multiple members. For example, $R^1$ represents —H, —$CH_3$, or —$CH_2CH_3$. Each member may be combined with each other member to form additional sub-groups, e.g., —H and —$CH_3$; —$CH_3$ and —$CH_2CH_3$; and —H and —$CH_2CH_3$.

The instant invention further contemplates embodiments in which each element listed under one group may be combined with each and every element listed under any other group. For example, $R^1$ is identified above as independently representing —H, —$CH_3$, or —$CH_2CH_3$. $R^2$ is identified above as independently representing —H, —$CH_3$, —$CH_2CH_3$, —$CH_2OH$, —$CH_2SH$, —$SCH_3$, —$SCH_2CH_3$, —$OCH_3$, —$OCH_2CH_3$, —S-carbocycloalkyl, —O-carbocycloalkyl, —S-aryl, —O-aryl, —S-benzyl, —O-benzyl, or —C(O)NHCH₂aryl. Each element of $R^1$ (—H, —$CH_3$, or —$CH_2CH_3$) can be combined with each and every element of $R^2$ (—H, —$CH_3$, —$CH_2CH_3$, —$CH_2OH$, —$CH_2SH$, —$SCH_3$, —$SCH_2CH_3$, —$OCH_3$, —$OCH_2CH_3$, —S-carbocycloalkyl, —O-carbocycloalkyl, —S-aryl, —O-aryl, —S-benzyl, —O-benzyl, or —C(O)NHCH₂aryl). For example, in one embodiment, $R^1$ may be —$CH_3$ and $R^2$ may be —$OCH_3$. Alternatively, $R^1$ may be —H; and $R^2$ may be —$SCH_3$, etc. Similarly, a third group is Y, in which the elements are defined as O or S. Each of the above embodiments may be combined with each and every element of Y. For example, in the embodiment wherein $R^1$ is —$CH_2CH_3$; $R^2$ is —S-carbocycloalkyl; and Y is O (or any other chemical moiety within the element of Y).

With each group, it is specifically contemplated that any one of more members can be excluded. For example, if $R^2$ is defined as —H, —$CH_3$, —$CH_2CH_3$, —$CH_2OH$, —$CH_2SH$, —$SCH_3$, —$SCH_2CH_3$, —$OCH_3$, —$OCH_2CH_3$, —S-carbocycloalkyl, —O-carbocycloalkyl, —S-aryl, —O-aryl, —S-benzyl, —O-benzyl, or —C(O)NHCH₂aryl it is also contemplated that $R^2$ is defined as —H, —$CH_3$, —$CH_2CH_3$, —$CH_2SH$, —$SCH_3$, —$OCH_3$, —$OCH_2CH_3$, —O-carbocycloalkyl, —S-aryl, —S-benzyl, or —O-benzyl.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, for at least a week.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

In this specification, when a group that contains more than one structural isomer does not designate which isomer is intended, the group includes all isomers. For example, if a group is designated "piperidylethyl," the group includes y-(z-piperidyl)ethyl, wherein y represents 1 or 2 and z represents 1, 2, 3, or 4. Similarly, "morpholinylethyl" means y-(z-morpholinyl)ethyl, wherein y represents 1 or 2 and z represents 2, 3, or 4.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

A method of treating a condition, disorder or disease with a chemical compound or a chemical composition includes the use of the chemical compound or chemical composition in the manufacture of a medicament for the treatment of the condition, disorder or disease. A compound or a group of compounds said to be effective in treating a condition, disorder or disease includes the compound or group of compounds for use in treating the condition, disorder or disease.

EXAMPLES

Example 1

Invitro Antitumor Activity

The antiproliferative activity of compounds 1-4 was determined in the seven types of human cancer cell lines K562 (Chronic Myelogenous Leukemia, CML), HT-29 (colon), and HL-60 (Acute Myloid Leukemia, AML), DU-145 (prostate), MCF-7 (breast), and GRANTA-519 (Mantle Cell Leukemia, MCL), and NSCL (non small cell lung carcinoma) and compared with cisplatin. The $IC_{50}$ values are listed in Table 3.

TABLE 3

| | | $IC_{50}$ (µM) for 1-4 and cisplatin | | | | |
|---|---|---|---|---|---|---|
| Cell Line | Tumor Type | Cmpd 1 | Cmpd 2 | Cmpd 3 | Cmpd 4 | Cisplatin |
| MCF-7 | Breast | 0.4 | 2.5 | 75 | 40 | 1.5 |
| DU145 | Prostate | 0.5 | 2.5 | 25 | 10 | 1.0 |
| H460 | NSCLC | 0.75 | 5.0 | 70 | 30 | 0.75 |
| HT-29 | Colon | 0.5 | 5.0 | >100 | 30 | 3.0 |
| K562 | CML | 0.3 | 2.5 | 30 | 50 | 1.5 |
| HL-60 | AML | 0.1 | 0.75 | 25 | ND | 0.75 |
| GRANTA-519 | MCL | 0.075 | ND | ND | ND | 0.25 |

Compound 4* was only tested up to 25 µM due to solubility issues. Any number above 25 µM is an estimate based on the plot from 1-25 µM. ND: Not Determined.

Figure 3:
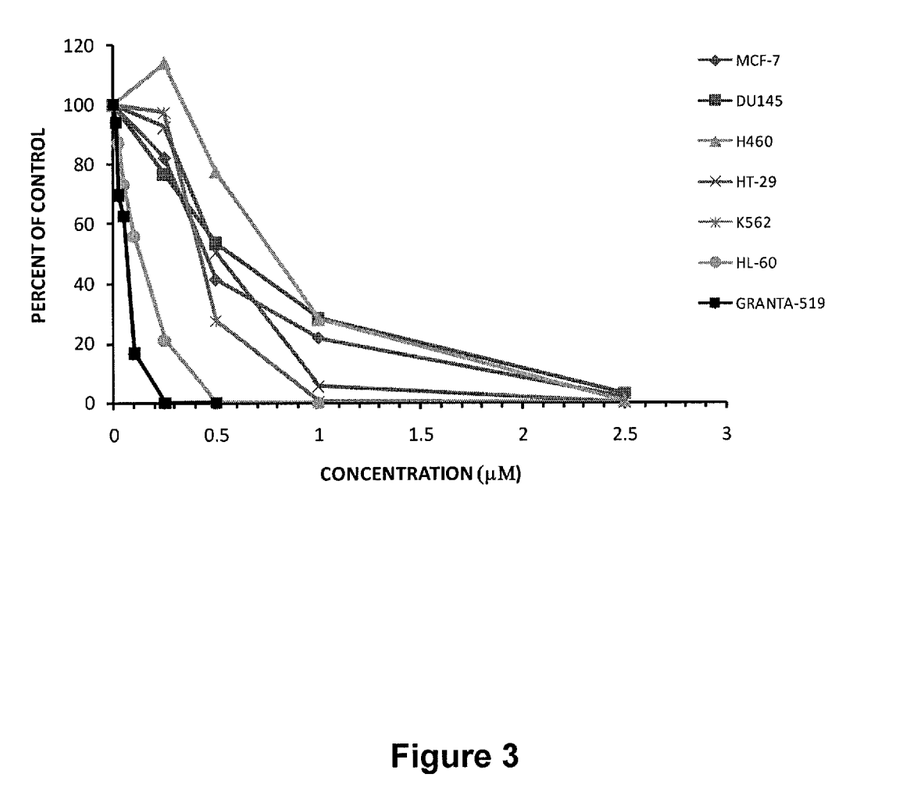
FIG. 3 is a dose response assay for Compound 1.
Figure 4:
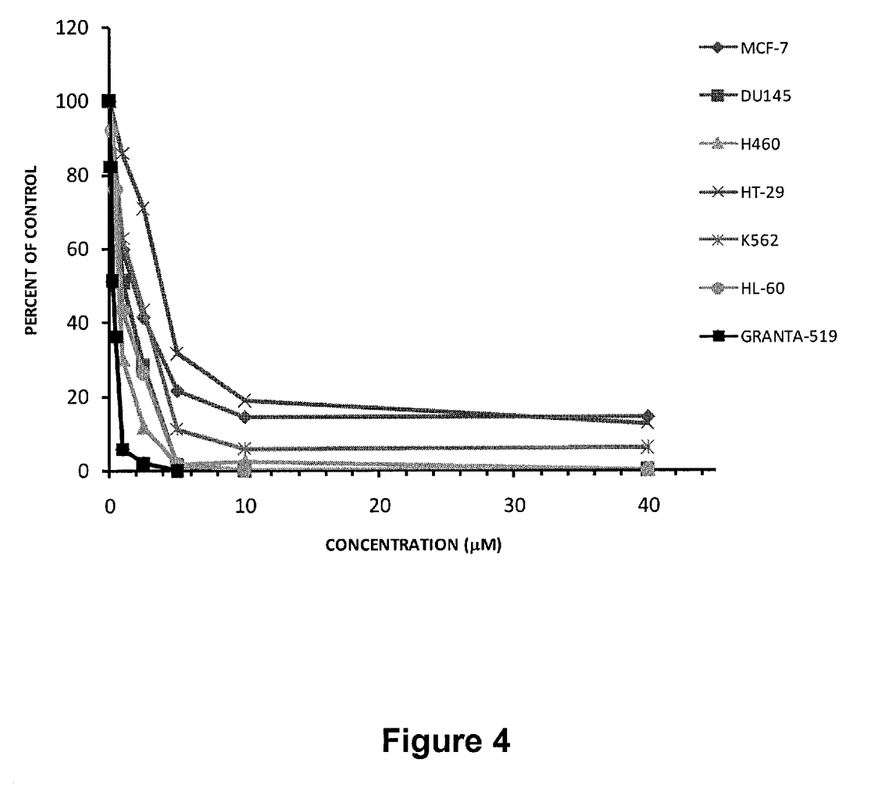
FIG. 4 is a dose response assay for Cisplatin.

Human cancer cells were plated in twelve-well dishes at a cell density of $2.5 \times 10^4$ cells/ml/well. The cells were treated, in duplicate, 24 hours later with increasing concentrations of each compound or cisplatin from Sigma (Table 3). The total number of viable cells was determined after 96 hours later by cell counting by hemacytometer and trypan blue staining. The percentage of viable cells remaining was calculated as follows: number of viable cells (compound treated)/number of viable cells (DMSO treated)*100. Compound 1 dose response assay plot (FIG. 3) is the average percent viable cells of the treated compared to the vehicle (DMSO) treated cells. DU-145, MCF-7, HT-29, H460 cells were grown in DMEM and K562, HL-60, Granata-519 cells were grown in RPMI medium both supplemented with 10% FBS (cell Generation) and 1 unit penicillin. Cells were routinely grown and treated at 37° C. under 90% humidity. The $IC_{50}$ (50% growth inhibition as compared to DMSO treated control) values in micromoles were determined by extrapolation from the dose response curves. Dose response curves were generated by plotting the percentage of cells at each concentration versus concentration tested. Compound 1 was chosen to produce more detailed growth curves based on overall highest activity profile. Similarly, cells were treated at increasing concentrations of cisplatin and detailed growth curves were generated (FIG. 4). Thus the activity of compound 1 was compared to cisplatin.

Compound 1 was the most active among the four compounds with the over all highest activity profile (FIG. 3) and in fact, better profile than widely used anticancer drug cisplatin (FIG. 4).

The anticancer activity of compound 1 against K562 (Chronic Myelogenous Leukemia, CML), HT-29 (colon), and HL-60 (Acute Myloid Leukemia, AML) human cancer cell lines is 5-7 times higher than cisplatin; the activity for DU-145 (prostate), MCF-7 (breast), and GRANTA-519 (Mantle Cell Leukemia, MCL) is 2-3 times higher more potent than cisplatin; and, the activity against NSCL (non small cell lung carcinoma) is the same as cisplatin. The substitution of a CO group in 1 with triphenylphosphine (compound 2) shows lower toxicity among seven types of cancer cell lines tested. The diphenylphosphinomethane and diphenylphosphino bridged dimers of ruthenium-maltol complexes 3-4 shows reduced activity when compared to monomeric ruthenium-maltol containing triphenylphosphine, 2. The cytotoxicity decreases with increase in the chain length of the phosphine bridged spacer from $IC_{50}$ values in the 25-100 µM range in all the cell lines tested (Table 1), indicating the spacer length activity relationships. Compound 4 was only tested up to 25 µM due to solubility issues; any number above 25 µM is an estimate based on the plot from 1-25 µM. The possible mechanism of action is due to in situ dissociation of a CO ligand from a ruthenium atom not bound by maltols generating a coordinatively unsaturated site for binding with the cellular targets perhaps serine/threonine kinases, guanine/adenine bases of DNA[23] and induction of apoptosis.

Example 2

Synthesis of Compounds

General Procedures

All operations were carried out under pure argon or nitrogen with the use of Schlenk techniques. The solvents were purified and distilled under an argon or nitrogen atmosphere. Thin layer chromatography was carried out using silica gel plates with plastic backs. Preparative thin layer chromatography was carried out using Analtech 0.5 mm silica gel 60 Å $F_{254}$ plates. Infrared spectra were recorded on a Nicolet Impact 400 FT-IR spectrometer as dichloromethane solution in 0.5 mm path length KBr cells. $^1$H NMR spectra were recorded using Bruker 400 MHz NMR spectrometer at St. Johns University and Kingsborough College/CUNY using $CD_2Cl_2$, $CDCl_3$ and referenced to the residual solvent peak. Mass spectra were recorded on an Agilent 6200 and 6210 LCMS-TOF instrument run in the multimode optimized for both ESI and APCI together at University of California, Riverside. Elemental analysis was carried out by using Perkin-Elmer 2400 Elemental Analyzer at Quantitative Technologies Inc., New Jersey.

A. Synthesis of $[Ru_3(CO)_8(C_{12}H_{10}O_6)]$, 1.

$Ru_3(CO)_{12}$ (639.34 mg, 1.0 mmol) and maltol (2-methyl-3-hydroxy-4-pyrone) (252.22 mg, 2.0 mmol) were added to a two-necked 100-mL round bottom flask under inert atmosphere. 25 mL of degassed anhydrous octane was added under argon atmosphere and the solution was refluxed gently for 3 days. The insoluble light yellow solid from the reaction mixture was filtered using a frit. The solid in the frit was washed with hexanes (3×10 mL) to remove traces of $Ru_3(CO)_{12}$. Alternatively, the product was also purified by silica gel column chromatography by eluting with dichloromethane. The solid thus obtained weighed to give 720 mg, (92.6%) based on $Ru_3(CO)_{12}$; m.p. 185-195° C. (dec). Single crystals were grown from solutions of diethyl ether containing few drops of methylene chloride at −10° C. Spectroscopic data for 1: IR ($CH_2Cl_2$): υ(C—H) 3052 (m), 2958 (w), 2858 (w); ν(terminal CO): 2091 (s), 2020 (s, sh), 1926 (s), 2030 (s); ν(C—O) due coordinated maltol ligands: 1615 (s), 1574 (s), 1510 (s). $^1$H NMR: ($CD_2Cl_2$): δ 7.61 (d, 2H, $^3J_{C-H}$=5 Hz), 6.26 (d, 2H, $^3J_{C-H}$=5 Hz), 2.53 (s, 6H). ESI-APCI mass spectrum calculated for $C_{20}H_{10}O_{14}Ru_3$, 777.4950 [M$^+$]; Found: 779.7302 [M+2H]$^+$, 694.7239 [M$^+$−3CO). Analytical calculated for $C_{20}H_{10}O_{14}Ru_3$, C, 30.90%; H, 1.30%. Found: C, 31.02%; H, 1.13%.

B. Synthesis of $[Ru_3(CO)_7(C_{12}H_{10}O_6)(PPh_3)]$, 2.

To a 50-mL schlenk flask under nitrogen atmosphere was added yellow solid compound 1 (25 mg, 0.035 mmol) followed by 7.0 mL of anhydrous degassed dichloromethane and stirred at room temperature. To the yellow solution was added solid $PPh_3$ (9.26 mg, 0.035 mmol). Immediately, the yellow color changed to dark red. Immediately, solid $Me_3NO.2;H_2O$ (2.0 mg, 0.018 mmol) was added at once. The dark-red solution changed to yellow solution after an hour and it was stirred for an additional 4 h. The thin layer chromatography indicated the formation of the product and some unreacted starting material. The compound 2 was purified by preparative thin layer chromatography using $CH_2Cl_2$. The compound 2 weighed to give 21 mg (64.9%) based on compound 1. Single crystals were grown from solutions of dichloromethane and hexanes at −10° C. Spectroscopic data for 2: IR ($CH_2Cl_2$): ν(C—H) several bands due to maltol ligand and triphenyl phosphine 3052 (m), 2958 (w), 2858 (w); ν(terminal CO): 2045 (w), 1991 (vs), 1970 (s), 1913 (m); ν(C—O) due to coordinated maltol ligands: 1616 (m), 1578 (w), 1513 (w). $^1$H NMR: ($CD_2Cl_2$): δ 7.62 (m, 6H), 7.56 (t, 2H), 7.42 (m, 9H), 6.21 (d, 1H, $^3J_{C-H}$=5 Hz), 6.17 (d, 1H, $^3J_{C-H}$=5 Hz), 2.54 (s, 6H). $^{31}$P NMR ($CD_2Cl_2$): δ 30.20 (s, $PPh_3$). ESI-APCI mass spectrum calculated for $C_{37}H_{25}O_{13}PRu_3$, 1011.7714, Found: 1012.8164 [MH]$^+$, 831.8022 [M$^+$−(one maltol+2CO)]. Analytical calculated for $C_{37}H_{25}O_{13}PRu_3$, C, 43.92%; H, 2.49%. Found: C, 44.12%; H, 2.61%.

C. Synthesis of $[Ru_3(CO)_6(C_{12}H_{10}O_6)(dppm)]$, 3.

To a 100-mL schlenk flask under nitrogen atmosphere was added yellow solid compound 1 (50 mg, 0.064 mmol) followed by 10.0 mL of anhydrous degassed $CH_2Cl_2$ and stirred at room temperature. To the yellow solution solid bis(diphenylphosphinomethane) (dppm) (12.30 mg, 0.032 mmol) was added. Immediately the yellow color changed to dark red.

Then the solid Me$_3$NO.2; H$_2$O (7.10 mg, 0.064 mmol) was added in one portion. The dark-red solution gradually changed to yellow solution over 30 minutes and it was stirred for additional 3 h. The thin layer chromatography indicated the formation of product and unreacted starting material 1. The compound 3 was purified by preparative thin layer chromatography (PTLC) using CH$_2$Cl$_2$ and methanol (95:5). The PTLC showed a top major yellow band due to the product and the bottom minor and unidentified yellow band. The yield of the product was 25 mg (41.6%) based on compound 1. Spectroscopic data for 3: IR (CH$_2$Cl$_2$): ν(C—H) several peaks for maltol and phosphine 3052 (m), 2958 (w), 2858 (w); ν(terminal CO) carbonyl stretching: 2047 (w), 1992 (vs), 1979 (s), 1914 (m); ν(C—O) due coordinated maltol ligands: 1616 (m), 1578 (w), 1515 (w). $^1$H NMR: (CD$_2$Cl$_2$): δ 7.56 (d, 4H, $^3J_{C-H}$=5 Hz), 7.45 (m, 8H), 7.14 (m, 12H), 6.20 (d, 4H), 6.20 (d, 2H, $^3J_{C-H}$=5 Hz), 4.15 (t, 2H, PCH$_2$P), 2.54 (s, 6H, 2CH$_3$), 2.47 (s, 6H, 2CH$_3$). $^{31}$P NMR (CD$_2$Cl$_2$): δ 23.40, 23.09. ESI-APCI mass spectrum calculated for C$_{63}$H$_{42}$O$_{26}$P$_2$Ru$_6$, 1883.3595 [M$^+$]; Found: 1883.5659 [M$^+$]. Analytical calculated for C$_{63}$H$_{42}$O$_{26}$P$_2$Ru$_6$, C, 40.18%; H, 2.25%. Found: C, 40.32%; H, 2.34%.

D. Synthesis of [Ru$_3$(CO)$_6$(C$_{12}$H$_{10}$O$_6$)(dppe)], 4.

To a 100-mL schlenk flask under nitrogen atmosphere was added yellow solid compound 1 (50 mg, 0.026 mmol) followed by 10.0 mL of anhydrous degassed CH$_2$Cl$_2$. To the yellow solution was added solid 1,2-bis(diphenylphosphinoethane) (dppe) (12.75 mg, 0.064 mmol). Immediately, the yellow color changed to dark red and then the solid Me$_3$NO.2; H$_2$O (7.1 mg, 0.062 mmol) was added. The dark red solution changed to yellow solution after half an hour and it was stirred for an additional 3 h. Thin layer chromatography indicated the formation of product top major yellow band, minor bottom yellow, and unreacted starting material. The top major band compound 4 was purified by preparative thin layer chromatography using CH$_2$Cl$_2$ and methanol (9.5:0.5). Yield: 15.0 mg (24.7%) based on compound 1. Spectroscopic data for 4: IR (CH$_2$Cl$_2$): ν(C—H) several bands due to maltol and phosphine 3052 (m), 2958 (w), 2858 (w); ν(terminal CO): 2047 (w), 1989 (vs, sh), 1970 (s), 1911 (m); ν(C—O) due coordinated maltol ligands: 1616 (m), 1578 (w), 1512 (w). $^1$H NMR (CDCl$_3$): δ 7.50 (d, 4H, a hydrogen at C6 next to ring oxygen from each of four maltol ligands, $^3J_{C-H}$=5 Hz), 7.42 (m, 20H, four phenyl groups from dppe, PPh$_2$CH$_2$CH$_2$PPh$_2$), 6.14 (d, 4H, $^3J_{C-H}$=5 Hz, a hydrogen at C5 from each of four maltol ligands), 3.43-3.72 (m, 4H, PCH$_2$CH$_2$P), 2.43 (s, 12H, 6CH$_3$ from four maltol ligands). $^{31}$P NMR (CDCl$_3$): δ 23.82, 23.79 (m, 4H). ESI-APCI mass spectrum calculated for: C$_{64}$H$_{44}$O$_{26}$P$_2$Ru$_6$, 1897.3861 [M$^+$]; Found: 1897.5847 [M]$^+$. Analytical calculated for C$_{64}$H$_{44}$O$_{26}$P$_2$Ru$_6$, C, 40.51%; H, 2.34%. Found: C, 40.55%; H, 2.29%.

Example 3

Crystallographic Analyses

Yellow single crystals of 1 suitable for diffraction analysis were grown by slow evaporation of solvent from solutions of pure compound in a diethyl ether-dichloromethane solvent mixture at −10° C. Red single crystals of 2 were grown by slow evaporation of solvent from dichloromethane-hexanes solution at −10° C. The data crystals used in the analyses were glued onto the end of a thin glass fiber. X-ray data were collected on a Bruker Kappa APEX-II CCD-based diffractometer, using Mo Kα radiation (0.71073 Å) at 298 K. The raw data frames were integrated with the SAINT+ program using a narrow-frame integration algorithm.[25] Corrections for the Lorentz and polarization effects were also applied by using the program SAINT. An empirical absorption correction based on the multiple measurements of equivalent reflections was applied by using the multi-scan method (SADABS).[26] Structure was solved by a combination of direct methods and different Fourier syntheses and was refined by full-matrix least-square on F$^2$, by using the SHELXTL software package.[27] All nonhydrogens were refined with anisotropic thermal parameters. The hydrogen atoms were placed in geometrically idealized positions and included as standard riding atoms during least-square refinements. Crystal data, data collection parameters, and results of analysis are listed in Table 4.

TABLE 4

Crystallographic Data for Compounds 1 and 2

|  | 1 | 2 |
| --- | --- | --- |
| empirical formula | C$_2$H$_{10}$O$_{14}$Ru$_3$ | C$_{37}$H$_{25}$O$_{13}$P$_1$Ru$_3$•0.5CH$_2$Cl$_2$ |
| formula weight | 777.49 | 1054.21 |
| temperature (K) | 298(2) | 296(2) |
| λ(Mo Kα), Å | 0.71073 | 0.71073 |
| μ | 1.914 mm$^{-1}$ | 1.255 mm$^{-1}$ |
| crystal system, | Orthorhombic, | Triclinic |
| space group | Pbca | P1 |
| lattice parameters |  |  |
| a, (Å) | 15.0395(4) | 11.6319(3) |
| b, (Å) | 11.5659(3) | 11.7082(3) |
| c, (Å) | 13.9525(4) | 15.7319(4) |
| α, (°) | 90 | 76.1310(10) |
| β, (°) | 90 | 82.9100(10) |
| γ, (°) | 90 | 82.3980(10) |
| V (Å$^3$) | 2426.97(11) | 2052.38(9) |
| Z | 4 | 2 |
| ρ$_{calc}$ (g/cm$^3$) | 2.128 | 1.706 |
| absorption coefficient (mm$^{-1}$) | 1.914 | 1.255 |
| F(000) | 1496 | 1038 |
| crystal size, mm$^3$ | 0.40 × 0.03 × 0.03 | 0.5 × 0.3 × 0.2 |
| θ range for data collection (°) | 4.05 to 30.05 | 1.34 to 30.53 |
| index ranges | −21 <= h <= 21, | −16 <= h <= 14, |
|  | −16 <= k <= 13, | −12 <= k <= 16, |
|  | −19 <= l <= 19 | −15 <= l <= 22 |

TABLE 4-continued

Crystallographic Data for Compounds 1 and 2

| | 1 | 2 |
|---|---|---|
| no. reflections collected | 32855 | 16735 |
| no. unique reflections | 3555 | 11897 |
| | [R(int) = 0.0300] | [R(int) = 0.0198] |
| | [I > 3σ(I)] | |
| No. of parameters | 169 | 524 |
| completeness to | θ = 30.05°; 99.5% | θ = 30.05°; 94.8% |
| absorption correction | multiscan | multi-scan |
| extinction coefficient | none | none |
| max. and min. transmission | 1.00 and 0. | 0.7461 and 0.6143 |
| Refinement method | Full-matrix least-squares on $F^2$ | Full-matrix least-squares on $F^2$ |
| data/restraints/parameters | 3555/0/169 | 11897/0/524 |
| goodness-of-fit (GOF)$^a$ on $F^2$ | 1.119 | 1.058 |
| final R indices [I > 3σ(I)] | R1 = 0.0182, wR$_2$ = 0.0409 | R1 = 0.0404, wR2 = 0.1155 |
| R indices (all data) | R1 = 0.0291, wR$_2$ = 0.0466 | R1 = 0.0568, wR2 = 0.1321 |
| largest diff. peak and hole (e$^-$/Å$^{-3}$) | 0.301 and −0.445 | 1.890 and −0.915 |

$^a$ R = $\Sigma_{hkl}(||F_{obs}| - |F_{calc}||)/\Sigma_{hkl}|F_{obs}|$; R$_w$ = $[\Sigma_{hkl}w(|F_{obs}| - |F_{calc}|)^2/\Sigma_{hkl}wF_{obs}^2]^{1/2}$, w = $1/\sigma^2(F_{obs})$; GOF = $[\Sigma_{hkl}w(|F_{obs}| - |F_{calc}|)^2/(n_{data} - n_{vari})]^{1/2}$.

Compound 1 crystallized in the orthorhombic crystal system and systematic absences consistent with space group Pbcn. Compound 2 crystallized in the triclinic crystal system. The space group P$\bar{1}$ was assumed and confirmed by the successful solution and refinement of the structure. Half molecule of dichloromethane from the crystallization solvent was co-crystallized in the asymmetric unit.

Citation List 1. (a) Gasser, G.; Ott, I.; and Metzler-Nolte, N. Organometallic anticancer compounds. *J. Med. Chem.* 2011, 54, 3-25. (b) Suss-Fink, G. Arene ruthenium complexes as anticancer agents. *Dalton Trans.* 2010, 39, 1673-1688.
2. Bratsos, I.; Jedner, S.; Gianferrara, T.; Alessio, E. Ruthenium anticancer compounds: challenges and expectations. *Chimia* 2007, 61, 692-697. (4) Jakupec, M. A.; Galanski, M.; Anion, V. B.; Hartinger, C. G.; Keppler, B. K. Antitumor metal compounds: more than theme and variations. *Dalton Trans.* 2008, 183-194. (5) Ott, I.; Gust, R. Non platinum metal complexes as anti-cancer drugs. *Arch. Pharm.* 2007, 340, 117-126. (6) Yan, Y. K.; Melchart, M.; Habtemariam, A.; Sadler, P. J. Organometallic chemistry, biology and medicine: ruthenium arene anticancer complexes. *Chem. Commun.* 2005, 4764-4776.
3. (a) Levina, A.; Mitra, A.; Lay, P. A. Recent developments in ruthenium anticancer drugs. *Metallomics* 2009, 1, 458-470. (b) Bruijnincx, P. C.; Sadler, P. J. Controlling platinum, ruthenium, and osmium reactivity for anticancer drug design. In *Adv. Inorg. Chem.*, van Eldik, R., Hubbard, C. D., Eds.; Elsevier: Amsterdam, 2009, pp 1-62. (c) Bruijnincx, P. C.; Sadler, P. J. New trend for metal complexes with anticancer activity. *Curr. Opin. Chem. Biol.* 2008, 12, 197-206. (d) Ang, W. H.; Dyson, P. J. Classical and nonclassical ruthenium-based anticancer drugs: towards targeted chemotherapy. *Eur. J. Inorg. Chem.* 2006, 20, 4003-4018. (e) Clarke, M. J. Ruthenium metallopharmaceuticals. *Coord. Chem. Rev.* 2003, 236, 209-233. (f) Clarke, M. J.; Zhu, F.; Frasca, D. R. Non-platinum chemotherapeutic metallopharmaceuticals. *Chem. Rev.* 1999, 99, 2511-2534.
4. (a) Peacock, A. F. A.; Sadler, P. J. Medicinal organometallic chemistry: designing metal arene complexes as anticancer agents. *Chem. Asian J.* 2008, 3, 1890-1899. (b) Dougan, S. J.; Sadler, P. J. The design of organometallic ruthenium arene anticancer agents. *Chimia* 2007, 61, 704-715. (c) Yan, Y. K.; Melchart, M.; Habtemariam, A.; Sadler, P. J. Organometallic chemistry, biology and medicine: ruthenium-arene anticancer complexes. *Chem. Commun.* 2005, 4764-4776. (d) Chen, H.; Parkinson, J. A.; Morris, R. E.; Sadler, P. J. Highly selective binding of organometallic ruthenium ethylenediamine complexes to nucleic acids: novel recognition mechanisms. *J. Am. Chem. Soc.* 2003, 125, 173-186.
5. (a) Bergamo, A.; Masi, A.; Dyson, P. J.; Sava, G. Modulation of the metastatic progression of breast cancer with an organometallic ruthenium compound. *Int. J. Oncol.* 2008, 33, 1281-1289. (b) Vock, C. A.; Renfrew, A. K.; Scopelliti, R.; Juillerat-Jeanneret, L.; Dyson, P. J. Influence of the diketonato ligand on the cytotoxicities of [Ru(η6-pcymene)-(R2acac)(PTA)]p complexes (PTA=1,3,5-triaza-7-phosphaadamantane). *Eur. J. Inorg. Chem.* 2008, 1661-1671. (c) Dyson, P. J. Systematic design of a targeted organometallic antitumor drug in preclinical development. *Chimia* 2007, 61, 698-703.
6. (a) Grguric-Sipka, S.; Stepanenko, I. N.; Lazic, J. M.; Bartel, C.; Jakupec, M. A.; Anion, V. B.; Keppler, B. K. Synthesis, X-ray diffraction structure, spectroscopic properties and antiproliferative activity of a novel ruthenium complex with constitutional similarity to cisplatin. *Dalton Trans.* 2009, 3334-3339. (b) Nov_akov_a, O.; Nazarov, A. A.; Hartinger, C. G.; Keppler, B. K.; Brabec, V. DNA interactions of dinuclear Ru(II) arene antitumor complexes in cell-free media. *Biochem. Pharmacol.* 2009, 77, 364-374. (c) Mendoza-Ferri, M. G.; Hartinger, C. G.; Nazarov, A. A.; Kandioller, W.; Severin, K.; Keppler, B. K. Modifying the structure of dinuclear ruthenium complexes with antitumor activity. *Appl. Organomet. Chem.* 2008, 22, 326-332. (d) Mendoza-Ferri, M. G.; Hartinger, C. G.; Eichinger, R. E.; Stolyarova, N.; Jakupec, M. A.; Nazarov, A. A.; Severin, K.; Keppler, B. K. Influence of the spacer length on the in vitro anticancer activity of dinuclear ruthenium-arene compounds. *Organometallics* 2008, 27, 2405-2407.
7. (a) Das, S.; Sinha, S.; Britto, R.; Somasundaram, K.; Samuelson, A. G. Cytotoxicity of half sandwich ruthenium(II) complexes with strong hydrogen bond acceptor ligands and their mechanism of action. *J. Inorg. Biochem.* 2010, 104, 93-104. (b) Meggers, E.; Atilla-Gokcumen, G. E.;

Grundler, K.; Frias, C.; Prokop, A. Inert ruthenium half-sandwich complexes with anticancer activity. *Dalton Trans.* 2009, 10882-10888. (c) Camm, K. D.; El-Sokkary, A.; Gott, A. L.; Stockley, P. G.; Belyaeva, T.; McGowan, P. C. Synthesis, molecular structure. *Dalton Trans.* 2009, 10914-10925. (d) Ruiz, J.; Vicente, C.; de Haro, C.; Bautista, D. A novel ruthenium(II) arene based intercalator with potent anticancer activity. *Dalton Trans.* 2009, 5071-5073.

8. Jakupec, M. A.; Galanski, M.; Anion, V. B.; Hartinger, C. G.; Keppler, B. K. Antitumour metal compounds: more than theme and variations. *Dalton Trans.* 2008, 2, 183-194.

9. (a) Kelland, L. The resurgence of platinum-based cancer chemotherapy. *Nat. Rev. Cancer* 2007, 7, 573-584. (b) Siddik, Z. H. Cisplatin: mode of cytotoxic action and molecular basis of resistance. *Oncogene* 2003, 22, 7265-7279.

10. Wang, D.; Lippard, S. J. Cellular processing of platinum anticancer drugs. *Nat. Rev. Drug Discovery* 2005, 4, 307-320.

11. Dyson, P. J.; Sava, G. Metal-based antitumour drugs in the postgenomic area. *Dalton Trans.* 2006, 1929-1933.

12. Reddy, V. D. Synthesis, characterization, and reactivity of a novel ruthenium carbonyl cluster containing tri-O-benzyl-D-glucal as a chiral carbohydrate ligand. *J. Organomet. Chem.* 2006, 691, 27-34.

13. Reddy, V. D.; Dayal, D.; Cosenza, S. C.; Reddy, M. V. R.; Pearl, Jr. W. C.; Adams, R. D. Glycal-ruthenium carbonyl clusters: Synthesis, characterization, and anticancer activity. *J. Organomet. Chem.* 2009, 694, 959-967.

14. Kahn, V.; Schved, F.; Lindner, P. Effect of maltol on the oxidation of 0-hydroxy phenols by mushroom tyrosinase and by sodium periodate. *Journal of Food Biochemistry*, 1993, 17, 217-233.

15. Maxton, D. G.; Thompson, R. P. H. Absorption of iron from ferric hydroxypyranone complexes. *British Journal of Nutrition.* 1994, 71, 203-207.

16. (a) Kandioller, W.; Hartinger, C, G.; Nazarov, A. A.; Kuznetsov, M. L.; John, R. O.; Bartel, C.; Jakupec, M. A.; Anion, V. B.; Dyson, P. J.; Keppler, B. K. Tuning the anticancer activity of maltol-derived ruthenium complexes by derivatization of the 3-hydroxy-4-pyrone moiety. *J. Organomet. Chem.* 2009, 694, 922-929. (b) Kandioller, W.; Hartinger, C, G.; Nazarov, A. A.; Kuznetsov, M. L.; Kasser, J.; John, R. O.; Bartel, C.; Jakupec, M. A.; Anion, V. B.; Keppler, B. K. From pyrone to thiopyrone ligands-rendering maltol-derived ruthenium(II)-arene complexes that are anticancer active in vitro. *Organometallics,* 2009, 28, 4249-4251.

17. (a) Duckett, S. B.; Wood, N. J. Parahydrogen-based NMR methods as a mechanistic probe in inorganic chemistry. *Coord. Chem. Rev.* 2008, 252, 2278-2291. (b) Aime, S.; Dastru, W.; Gobetto, R.; Russo, A.; Viale, A.; Canet, D. A novel application of para $H_2$: the reversible addition/elimination of $H_2$ at a $Ru_3$ cluster revealed by the enhanced NMR emission resonance from molecular hydrogen. *J. Phys. Chem. A.* 1999, 103, 9702. (c) Aime, S.; Dastru, W.; Gobetto, R.; Reineri, F.; Russo, A.; Viale, A. Investigating pathways of molecular $H_2$ exchange in $(\mu-H)_2Os_3(CO)_{10}$. *Organometallics* 2001, 20, 2924. (d) Blazina, D.; Duckett, S. B.; Dyson, P. J.; Johnson, B. F. G.; Lohman, J. A. B.; Sleigh, C. J. *J. Am. Chem. Soc.* 2001, 123, 9760. (e) Weller, A. S.; McIndoe, J. S. Reversible binding of dihydrogen in multimetallic complexes. *Eur. J. Inorg. Chem.* 2007, 4411-4423. (f) Prestwich, T. G.; Blazina, D.; Duckett, S. B.; Dyson, P. J. A parahydrogen study of catalytic hydrogenation by diphosphane-substituted triruthenium clusters. *Eur. J. Inorg. Chem.* 2004, 4381-4387.

18. Leong, W. K.; Lin, Q. Reaction of pyrones with triosmium clusters. *Organometallics,* 2003, 22, 3639-3648.

19. Zeng, T. C.; Cullen, W. R.; Rettig, S. J. Multinuclear Complexes Derived from Ferrocenylphosphines and triruthenium dodecacarbonyl. *Organometallics* 1994, 13, 3594-3604.

20. Gastel, F. V.; Corrigan, J. F.; Doherty, S; Taylor, N. J; Carty, A. J. Facile and Quantitative Activation of Dihydrogen by the Phosphinidene-Stabilized Cluster $Ru_4(CO)_{13}$ $(\mu_3\text{-PPh})$: Synthesis and spectroscopic and structural characterization of $(\mu-H)_2Ru_4(CO)_{12}(\mu_3\text{-PPh})$. *Inorg. Chem.* 1992, 31, 4492-4498.

21. Adams, R. D.; Captain, B.; Fu. W. Oxidative addition of silanes to $Ru_5(CO)_{15}(\mu_5\text{-C})$ under photolytic conditions. The synthesis and structural characterizations of $Ru_5(CO)_{14}(SiEt_3)(\mu_5\text{-C})(\mu\text{-H})$ and $Ru_5(CO)_{15}(SiEt_3)(\mu_5\text{-C})(\mu\text{-H})$. *Organometallics* 2000, 19, 3670-3673.

22. Andreu, P. L.; Cabeza, J. A.; Ri'o, I.; Riera, V. Synthesis and reactivity of triruthenium carbonyl cluster complexes containing a bridging 1-azavinylidene ligand derived from benzophenoneimine *Organometallics* 1996, 15, 3004-3010.

23. Gossens, C.; Tavernelli, I.; Rothlisberger, U. DNA structural distortions induced by Ruthenium-arene anticancer compounds. *J. Am. Chem. Soc.,* 2008, 130, 10921-10928.

24. Casini, A.; Gabbiani, C.; Sorrentino, F.; Pia Rigobello, M.; Bindoli, A.; Geldbach, T. J.; Marrone, A.; Re, N.; Hartinger, C. G.; Dyson, P. J.; Messori, L. Emerging Protein Targets for Anticancer Metallodrugs: Inhibition of Thioredoxin Reductase and Cathepsin B by Antitumor Ruthenium(II)-Arene Compounds. *J. Am. Chem. Soc.* 2008, 51, 6773-6781.

25. SAINT+ version 6.22a; Bruker Analytical X-ray System, Inc., Madison, Wis., 2001

26. Sheldrick, G. M., SADABS version 2.0; Bruker Analytical X-ray System, Inc., Madison, Wis., 2007.

27. Sheldrick, G. M. SHELXTL, version 5.0; Siemens Analytical Instruments, Inc., Madison, Wis., 1994.

I claim:

1. An anti-cancer ruthenium complex having formula 1:

wherein:

$R^1$ independently represents —H, —$CH_3$, or —$CH_2CH_3$;
$R^2$ independently represents —H, —$CH_3$, —$CH_2CH_3$, —$CH_2OH$, —$CH_2SH$, —$SCH_3$, —$SCH_2CH_3$, —$OCH_3$, —$OCH_2CH_3$, —S-carbocycloalkyl, —O-carbocycloalkyl, —S-aryl, —O-aryl, —S-benzyl, —O-benzyl, or —C(O)NHCH$_2$aryl;

n independently represents 0 or 1;

when n represents 1, X independently represents O, S, or $NR^3$;

when n represents 0, a single bond exists between the two carbon atoms adjacent to (X)

$R^3$ independently represents —H, —$CH_3$, or —$CH_2CH_3$;

Y independently represents O or S

Z independently represents O, S, or $NR^4$:

$R^4$ independently represents —H or —$CH_3$;

L represents a carbonyl, $Ph_3P$, imidazole, thiazole, oxazole, or indazole moiety; or an N-heterocyclic carbene moiety selected from the group consisting of 1,3-imidazol-2-ylidene substituted independently at 1,3 atoms; 1,2,4-triazol-5-ylidene substituted independently at 1,4 atoms; or 1,2,3-triazol-5-ylidene substituted independently at 1,4 atoms; wherein the N-heterocyclic carbene moiety is substituted by a substituent selected independently from the group consisting of aryl, benzyl, $C_{1-6}$ alkyl, or cyclohexyl;

aryl is selected from the group consisting of phenyl or a 5 or 6 member heterocyclic aromatic ring comprising at least one ring heterocyclic atom or group selected from the group consisting of —O—, —S—, —NH—, or —$NCH_3$—;

carbocycloalkyl groups are 5 or 6 member non-aromatic carbocyclic rings;

aryl and carbocycloalkyl groups independently are unsubstituted, or are substituted at any position with one or more substituents;

aryl substituents independently are $R^{10}$, —$OR^{11}$, —$SR^{11}$, —$N(R^{11})_2$, $R^{10}C(O)$—, nitro, or halo (F, Cl, or Br), wherein $R^{10}$ independently represents aryl, $C_{1-6}$ alkyl or cyclohexyl; and $R^{11}$ independently represents H, aryl, $C_{1-6}$ alkyl or cyclohexyl; and carbocycloalkyl substituents independently are $C_{1-6}$ alkyl.

2. An anti-cancer ruthenium complex of claim 1, wherein L represents a carbonyl.

3. An anti-cancer ruthenium complex of claim 1, wherein Y is O.

4. An anti-cancer ruthenium complex of claim 1, wherein n is 1 and X is O.

5. An anti-cancer ruthenium complex of claim 1, wherein $R^1$ is —H or —$CH_3$.

6. An anti-cancer ruthenium complex of claim 1, wherein $R^1$ is —$CH_3$.

7. An anti-cancer ruthenium complex of claim 1, wherein $R^2$ is —H or —$CH_3$.

8. An anti-cancer ruthenium complex of claim 1, wherein $R^2$ is —H.

9. An anti-cancer ruthenium complex of claim 1, wherein Z is O.

10. An anti-cancer ruthenium complex of claim 1, wherein n is 1 and X is S.

11. An anti-cancer ruthenium complex of claim 1, wherein n is 1, X is O, Y is O, Z is O, $R^1$ is —$CH_3$, $R^2$ is —H, and L is carbonyl.

12. An anti-cancer ruthenium complex having formula 1:

wherein:

n is 1, X is O, Y is O, Z is O, $R^1$ is —$CH_3$, $R^2$ is —H, and L is carbonyl.

* * * * *

UNITED STATES PATENT AND TRADEMARK OFFICE
CERTIFICATE OF CORRECTION

PATENT NO. : 8,748,484 B2  
APPLICATION NO. : 14/110357  
DATED : June 10, 2014  
INVENTOR(S) : Varattur Dayal Reddy Page 1 of 1

It is certified that error appears in the above-identified patent and that said Letters Patent is hereby corrected as shown below:

IN THE SPECIFICATION:

Column 8, Line 63

Now Reads: "phosphmes"  
    Should Read: "phosphines"

Signed and Sealed this  
Ninth Day of September, 2014

Michelle K. Lee  
*Deputy Director of the United States Patent and Trademark Office*